United States Patent [19]

Baldwin

[11] Patent Number: 4,722,924

[45] Date of Patent: Feb. 2, 1988

[54] PEPTIDE SUBSTITUTED PENICILLINS

[75] Inventor: Jack E. Baldwin, Headington, England

[73] Assignee: National Research Development Corporation, England

[21] Appl. No.: 766,429

[22] Filed: Aug. 22, 1985

[30] Foreign Application Priority Data

Aug. 22, 1984 [GB] United Kingdom ............... 8421279

[51] Int. Cl.⁴ ............... A61K 31/43; C07D 499/48
[52] U.S. Cl. ............... 514/192; 435/43; 530/331; 540/334
[58] Field of Search ............... 540/334; 514/192

[56] References Cited

U.S. PATENT DOCUMENTS 3,142,673 7/1964 Hobbs ............... 540/313
3,466,275 9/1969 Morin et al. ............... 540/313

OTHER PUBLICATIONS

J. E. Baldwin et al., J.C.S. Chem. Comm., 1980, 1271–1273.
J. E. Baldwin et al., J.C.S. Chem. Comm., 1981, 246–247.
J. E. Baldwin et al., J.C.S. Chem. Comm., 1981, 917–919.
Shields et al., Helvetica Chimica Acta-vol. 67, Fasc 3, (1984), NR 97, pp. 870–875.
J. E. Baldwin et al., J.C.S. Chem. Comm., (1983), 1317–1320.

Primary Examiner—Werren B. Lone
Assistant Examiner—Vera C. Clarke
Attorney, Agent, or Firm—Jacobs & Jacobs

[57] ABSTRACT

A compound of formula I or a physiologically acceptable salt thereof

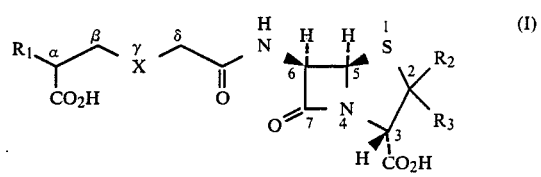

wherein X represents sulphur or methylene, $R_1$ represents hydrogen, amino or an acylated or carbamylated amino group, $R_2$ represents hydrogen or an alkyl group and $R_3$ represents an alkoxy group.

20 Claims, No Drawings

PEPTIDE SUBSTITUTED PENICILLINS

This invention relates to antibiotics and in particular to novel beta lactam antibiotics and their production.

The beta lactams constitute a group of antibiotics of particular interest into which considerable research has taken place with the aim of producing new antibiotic compounds.

The biosynthesis of isopenicillin N from D-valine, L-cysteine and L-α-amioadipic acid proceeds via the tripeptide δ-(L-α-aminoadipyl-L-cysteinyl-D-valine (throughout this specification "adipyl" is used to denote the monovalent radical derived from adipic acid) through the action on this tripeptide of the enzyme isopenicillin N synthetase. The action of isopenicillin N synthetase on the alternative tripeptides, δ-(L-α-aminoadipyl)-L-cysteinyl-D-isoleucine, δ-(L-α-aminoadipyl)-L-cysteinyl-D-alloisoleucine and δ-(L-α-aminoadipyl)-L-cysteinyl-D-(α-aminobutyrate) has been studied by Bahadur, Baldwin and Usher, J.A.C.S., 1981, 103, 7650, in order to evaluate the substrate specificity for this conversion but, although each of these peptides was converted by the enzyme to a penicillin molecule, and although such compounds are covered by UK Pat. No. 2052486A, these novel alkyl analogues of isopenicillin N showed a significantly lower specific bacterial activity than isopenicillin N itself. I have now found that it is possible by using a particular, carefully selected, group of novel tripeptides as the substrate for isopenicillin N synthetase to prepare novel antibiotic molecules having a generally higher specific bacterial activity than these earlier analogues.

Accordingly the present invention comprises a compound of the formula

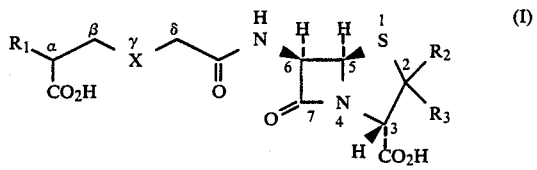

wherein X is sulphur or methylene, $R_1$ is hydrogen, amino or an acylated or carbamylated amino group, $R_2$ is hydrogen or an alkyl group and $R_3$ is an alkoxy group.

Such penicillin compounds (I) are of course very unusual in that they contain an alkoxy group and either hydrogen or an alkyl group at the 2-position of the penam system instead of the usual two alkyl (methyl) groups.

Among the penicillins (I), X is preferably a methylene group rather than sulphur. Compounds in which $R_1$ is amino or an acylated or carbamylated amino group are of particular interest. Substituted amino groups preferably have the form RCONH— or RNHCONH— where R is hydrogen or a lower ($C_1$ to $C_5$ and preferably $C_1$ to $C_3$) alkyl group, or alternatively a phenyl or substituted phenyl group. Such substituted phenyl groups may contain one or more of various types of substituent including alkyl and alkoxy groups, for example those being or containing alkyl groups of 1, 2 or 3 or more carbon atoms as described below for $R_2$ and especially methyl and methoxy, substituents being or containing a halogen residue, for example bromo, chloro and fluoro and halogen substituted alkyl groups such as $CF_3$, free and substituted amino groups, for example dimethylamino, hydroxy and nitro groups, as well as other benzene ring substituting groups known in the art. In general, however, compounds containing an unsubstituted amino group $R_1$ are of greater interest than those containing substituted amino groups.

As regards $R_2$, this is preferably an alkyl group and $R_2$ and also $R_3$ may conveniently each be separately selected from groups of 1 to 5 carbon atoms, especially of 1 to 3 or 4 carbon atoms. Such groups conveniently are or contain a straight chain alkyl group, the smaller groups such as isopropyl, propyl, particularly ethyl and especially methyl, and isopropoxy, propoxy, particularly ethoxy and especially methoxy, being most preferred.

It may be advantageous, for example in order to increase water solubility, for the penicillins (I) to be in the form of a physiologically aceeptable salt thereof. Such salt formation may involve the amino group and a physiologically acceptable inorganic or organic acid or one or both of the carboxyl groups and a physiologically acceptable inorganic or organic base, the sodium and potassium salts of the penicillin compounds (I), for example, being of some interest. As regards the stereochemistry of the penicillins (I), where $R_1$ is other than hydrogen there are two possible configurations at the asymmetric carbon atom to which the groups $R_1$ and $CO_2H$ are attached and it is preferred that this carbon atom is of the L configuration. In respect of $R_2$ and $R_3$, there are two possible configurations at the asymmetric carbon atom to which these groups are attached, depending on whether the group $R_2$ or the group $R_3$ is in a similar spatial dispostion to the adjacent carboxyl group. The latter alternative is of particular interest, especially in the case where $R_2$ is alkyl, since such an isomer is that directly generated by the process described herein, as discussed hereinafter in more detail.

Specific pencillins according to the present invention are the compounds (I) in which X is sulphur or methylene, $R_1$ is hydrogen or amino, $R_2$ is hydrogen, methyl or ethyl, and $R_3$ is methoxy or ethoxy, including particularly those compounds in which $R_2$ is hydrogen or methyl and $R_3$ is methoxy, such as the compounds 2-methoxy-2-methyl-6-δ-(L-α-aminoadipamido)-3-carboxypenam, 2-methoxy-2-methyl-6-δ-(D-α-aminoadipamido)-3-carboxypenam, 2-methoxy-2-methyl-6-δ-adipamido-3-carboxypenam and 2-methoxy-2-methyl-6-δ-(L-S-carboxymethylcysteinyl)-3-carboxypenam, 2-methoxy-6-δ-(L-α-aminoadipamido)-3-carboxypenam, 2-methoxy-6-δ-(D-α-aminoadipamido)-3-carboxypenam, 2-methoxy-6-δ-adipamido-3-carboxypenam and 2-methoxy-6-δ-(L-S-carboxymethylcysteinyl)-3-carboxypenam. These specific penicillins (I) are of particular interest, especially where they contain a group $R_2$ which is alkyl, as the stereoisomer in which the alkoxy and carboxy groups at the 2- and 3-positions of the thiazolidone ring have a similar spatial disposition, being in the cis configuration, i.e. as the alkoxy 2S-isomer. The structure of the compound 2S-2-methoxy-2-methyl-6-δ-(L-α-aminoadipamido)-3-carboxypenam is illustrated below in formula (II). In formula (II) the adjacent amino and carboxy groups are shown in the zwitterion form in which they usually exist.

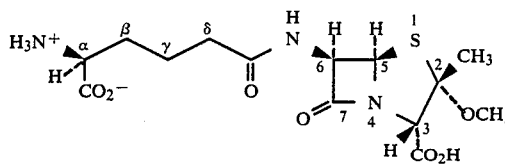

(II)

The penicillins (I) in which $R_1$ is hydrogen or amino may conveniently be prepared from the corresponding tripeptide of formula

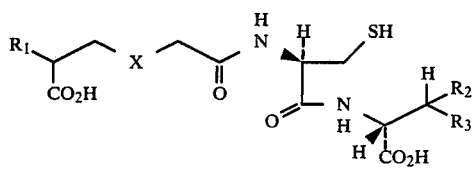

(III)

wherein X is sulphur or methylene, $R_1$ is hydrogen or amino, $R_2$ is hydrogen or an alkyl group and $R_3$ is an alkoxy group, through the action of the enzyme isopenicillin N synthetase. As regards the stereochemistry of the tripeptide, it is believed that, where the carbon atom to which the groups $R_1$ and $CO_2H$ are attached is asymmetric, the configuration at this atom is retained on conversion of the tripeptide (III) to the penicillin (I), the tripeptide used therefore conveniently having the same stereochemistry at this point as the penicillin. Irrespective of whether $R_2$ is hydrogen or an alkyl group the penicillin (I) can, as explained hereinbefore, exist in two stereoisomeric forms differing in the disposition of the groups at the $C_2$ position of the thiazolidone ring. When $R_2$ is an alkyl group, the tripeptide (III) will similarly contain an asymmetric carbon atom at the equivalent position and it has been found that efficient conversion of the tripeptide (III) to the penicillin (I) with isopenicillin N synthetase occurs only with the tripeptide having the R-configuration at the 2-position, this configuration being retained during the conversion to give the stereochemically equivalent penicillin having the S-configuration at the 2-position. When $R_2$ is hydrogen, the carbon atom at the equivalent position in the tripeptide is not asymmetric and it is believed that the penicillin obtained is a mixture of the two stereoisomeric forms differing at the $C_2$ position.

The tripeptides (III) used to prepare the penicillins (I) are novel compounds and are included within the scope of the present invention in their monomeric or disulphide form (tripeptides in the latter form are converted to the monomeric form by the use of dithiothreitol as described hereinafter) as are derivatives thereof in which one or more functional groups therein are in protected form. Thus, the sulphydryl group of the central cysteinyl residue, the carboxy group of the C-terminal residue, and the carboxy and amino (where present) groups of the N-terminal residue may be protected, for example by conventional protecting groups used in peptide chemistry and as illustrated in the Examples, such protected tripeptides being used in the synthesis of the final, unprotected tripeptide (III). Specific tripeptides according to the present invention are compounds (III) in which X is sulphur or methylene, $R_1$ is hydrogen or amino, $R_2$ is hydrogen, methyl or ethyl, and $R_3$ is methoxy or ethoxy, including particularly those compounds in which $R_2$ is hydrogen or methyl and $R_3$ is methoxy, such as the compounds δ-(L-α-aminoadipyl)-L-cysteinyl-(2R-2-amino-3-methoxybutanoic acid), δ-(D-α-aminoadipyl)-L-cysteinyl-(2R-2-amino-3-methoxybutanoic acid), δ-adipyl-L-cysteinyl-(2R-2-amino-3-methoxybutanoic acid), δ-(L-S-carboxymethylcysteinyl)-L-cysteinyl-(2R-2-amino-3-methoxybutanoic acid), δ-(L-α-aminoadipyl)-L-cysteinyl-(D-serine O-methyl ether), δ-(D-α-aminoadipyl)-L-cysteinyl-(D-serine O-methyl ether), δ-adipyl-L-cysteinyl-D-serine O-methyl ether) and δ-(L-S-carboxymethylcysteinyl)-L-cysteinyl-(D-serine O-methyl ether). In the case of those tripeptides having both an alkoxy and an alkyl group on the β-carbon atom of the C-terminal amino acid residue it is strongly preferred, for the reasons indicated previously, that this alkoxy group and the α-carboxy group are in the cis configuration. For the first group of four compounds named above a 2R,3R-2-amino-3-methoxybutanoic acid residue is therefore strongly preferred at the C-terminus. The structure of the compound δ-(L-α-aminoadipyl)-L-cysteinyl-(2R,3R-2-amino-3-methoxybutanoic acid) is illustrated below in formula (IV), the adjacent amino and carboxy groups being shown in the zwitterion form in which they usually exist.

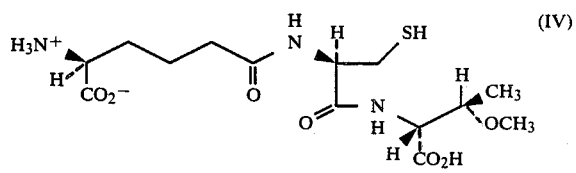

(IV)

The tripeptides (III) are readily synthesised by standard procedures of peptide chemistry. Thus a suitable route generally involves the coupling of protected forms of the individual amino acids constituting the tripeptide and subsequent deprotection. Suitable protecting groups may be selected from those routinely used in the art of peptide synthesis, for example amino groups being protected as benzyloxycarbonyl or like derivatives, carboxy groups as benzyl or other esters and sulphydryl groups as the benzyl derivative. Such a route is illustrated in the Example for the preparation of the tripeptides δ-(L-α-aminoadipyl)-L-cysteinyl(2R,3R-2 amino-3-methoxybutanoic acid) and δ-(L-α-aminoadipyl)-L-cysteinyl-(D-serine O-methyl ether).

For production of the penicillin compounds (1) the tripeptides (III) are subjected to the action of isopenicillin N synthetase. This enzyme is produced by various micro-organisms, for example *Penicillin chrysogenum* and *Streptomyces clavuligenis* but a preferred source is *Cephalosporium acremonium*. The micro-organism *C. acremonium* is widely available so that, apart from other sources, several strains are available from the American Type Culture Collection, for example ATCC 20339 (Cephalosporium sp. strain F.12), ATCC 14553 (*C. acremonium*) and ATCC 36255 (*Acremonium strictum*). The cells are cultured under suitable conditions and a cell free extract then procuded which may be purified by a combination of procedures known in the art for the purification of proteins. A suitable purification procedure is illustrated in the Examples and this will provide an enzyme suitable for use in conversion of the tripeptide to an antibiotic compound, generally providing a level of conversion of about 20% or higher for the tripeptides containing an alkyl group $R_2$. An enzyme of a level of purity such as it obtained by this procedure is free from activity which would extend the conversion beyond the isopenicillin stage. Incubation of the compound with the enzyme in an aqueous medium at a pH in the range from 7.0 to 8.0, for example 7.5, at a temperature in the range from 25°-28° C., for example 27° C., and for a period of 30 to 60 minutes, for example 30 minutes, is generally suitable, following which the antibiotic compound is isolated by the use of conventional procedures. In order to optimise the activity of the enzyme it is preferred to employ one or more cofactors, in particular one or more, and conveniently all three, of iron, especially ferrous ions as provided for example by ferrous sulphate, ascorbate ions as provided for example by ascorbic acid, and dithiothreitol. Catalase may also be incorporated with advantage into the incubation medium. A procedure using these added components is illustrated in the Examples.

Penicillins (I) containing an acylated or carbamylated amino group may conveniently be prepared from the corresponding penicillin (I) containing an amino group by the action of a suitable acylating agent, for example using the appropriate acid or a derivative thereof, such ad the chloride or anhydride, or of a suitable carbamylating agent, such as an appropriate alkali metal cyanate. Salts may conveniently be prepared using the appropriate inorganic or organic acid or base.

Penicillin compounds according to the present invention, particularly the penicillin 2S-2-methoxy-2-methyl-6-δ-(L-α-aminoadipamido)-3-carboxypenam and 2-methoxy-6-δ-(L-α-aminoadipamido)-3-carboxy penam have given very promising results in tests with *Staphylococcus aureus* and are also of interest for use in the control of a wide range of bacteria, both Gram-negative and Gram-positive, for example *Escherichia coli*, *Salmonella typhimurium* and *Bacillus magaterium*. Thus, a level of activity is observed which is at least comparable with that or isopenicillin N itself and it will be appreciated that these compounds therefor present a valuable alternative source of antibiotics.

The compounds may be formulated for use as pharmaceuticals, for veterinary or particularly for human use, by a variety of methods but usually involving the use of a physiologically acceptable diluent or carrier. For instance, they may be applied as an aqueous, oily or emulsified composition incorporating a liquid diluent which most usually will be employed for parenteral administration and therefore will be sterile and pyrogen free. Alternatively, the compound may be formulated with a liquid diluent for oral administration, although it is more usually preferred to use for this purpose compositions incorporating a solid carrier, for example a conventional solid carrier material such as starch, lactose, dextrin or magnesium stearate.

Compositions may be formulated in unit dosage form, i.e. in the form of discrete portions each comprising a unit dose, or a multiple or sub-multiple of a unit does. Whilst the dosage of active compound given will depend on various factors, including the particular compound which is employed in the composition, it may be stated by way of guidance that levels broadly similar to those used for existing penicillins may be employed, i.e. daily dosage levels for adult humans being of the order of 250 mg to 5 g, often 500 g to 2 g, usually divided, although levels both above and below this may also be used in some cases; doses for children and for veterinary use will generally be adapted on a similar mg/kg basis. Where desired, more than one compound according to the present invention may be administered in the pharmaceutical composition or, indeed, other active compounds may be included in the composition.

The invention thus includes a pharmaceutical composition comprising a compound (I) as described hereinbefore together with a physiologically acceptable diluent or carrier. Moreover, it also includes a method for the treatment of a patient suffering from a bacterial infection which comprises administering to that patient an amount of a compound (I) as described hereinbefore which is effective to counter that infection.

The invention is illustrated by the following Examples.

EXAMPLES

Example 1

Preparation of
δ-(L-α-aminoadipyl)-L-cysteinyl-(2R,3R-2-amino 3-methoxybutanoic acid)

(1) 2R,3R- and 2S,3S-2-Bromo-3-methoxybutanoic acid

Crotonic acid (8.6 g, 100 mmol) is dissolved in methanol (50 ml) and N-bromacetamide (13.8 g, 10 mmol) is added in portions over 30 minutes. The solution is stirred at 25° C. for 15 hours and the solvent is then evaporated and the residue partitioned between diethyl ether and water. The ether layer is dried ($Na_2SO_4$), filtered, evaporated and the residue distilled to yield the title compounds as a colourless oil (14.3 g, 72%), b.p. 88°-89°/0.5 mm.

(2) 2R,3R- and 2S,3S-2-Amino-3-methoxybutanoic acid 2R,3R- and 2S,3S-2-Bromo-3-methoxybutanoic acid (14 g, 71 mmol) are dissolved in ammonia (s.g. 0.88, 250 ml) and the mixture heated in an autoclave at 95° C. for 8 hours. The mixture is cooled to 25° C., evaporated, and the residue suspended in acetone. The resultant colourless solid is filtered off and washed with acetone to give the title compounds as a colourless solid containing residual ammonium bromide, (12.1 g) m.p. 180°-184° C. (dec.).

(3) 2R,3R- and 2S,3S-N-Benzyloxycarbonyl-2-amino-3-methoxybutanoic acid, benzyl ester 2R,3R- and 2S,3S-2-Amino-3-methoxybutanoic acid (3.1 g) are dissolved in a mixture of 1M sodium hydroxide (27 ml), water (20 ml), and dioxan (40 ml). Benzyl chloroformate (3.8 ml, 22 mmol) in dioxan (20 ml) and 1M sodium hydroxide (27 ml) are added to the solution individually, each at the same rate of addtion, over 25 minutes. The mixture is stirred for 1 hour, extracted into ethyl acetate (3×200 ml), acidified to pH 1 with 2N hydrochloric acid and then re-extracted into ethyl acetate (3×200 ml). The combined organic extracts are dried, filtered, and evaporated to give an oil. This oil is dissolved in dry dimethyl formamide (20 ml) and to the solution are added sodium hydrogen carbonate (3.14 g, 41 mmol), benzyl bromide (3.8 ml, 33 mmol), anhydrous sodium sulphate (200 mg) and sodium iodide (10 mg), the whole being stirred at 25° C. for 24 hours. The mixture is then extracted into dichloromethane (200 ml), washed with water (4×300 ml), dried (sodium sulphate), filtered and evaporated. Purification by chromatography on silica gel using ethyl acetate and petroleum ether as consecutive eluants gives the title compounds as a colourless oil (4.2 g, 65%) which solidifies on standing, m.p. 44° C.

(4) 2R,3R- and 2S,3S-2-Amino-3-methoxybutanoic acid, benzyl ester 2R,3R- and 2S,3S-N-Benzyloxycarbonyl-2-amino-3-methoxybutanoic acid, benzyl ester (500 mg, 1.4 mmol) are dissolved in dry dichloromethane (3 ml) and hydrobromic acid (45% in acetic acid, 2 ml) is added. The mixture is stirred under argon for 20 minutes and is then evaporated. The residue is dissolved in dichloromethane (3×3 ml) and re-evaporated (3×) to give a further residue which is dissolved in xylene (2×3 ml) and re-evaporated (2×). Petroleum ether (5 ml) is then added and the product is triturated for 5 minutes before discarding the mother liquor and dissolving the solid residue in dichloromethane (5 ml). Triethylamine (1 ml) is added to the dichloromethane solution which is then stirred for 2 minutes and evaporated. The residue is dissolved in dichloromethane (3×5 ml) and re-evaporated (3×) to give a further residue which is triturated with diethyl ether (5 ml). The resulting solid is filtered off, re-extracted with diethyl ether (2×5 ml) and the ethereal layers combined and evaporated to yield the title compounds as a colourless oil (290 mg, 93%).

(5) (N-Benzoyloxycarbonyl-α-benzyl-δ-L-aminoadipyl)-S-benzyl-L-cysteinyl-(2R,3R-2-amino-3-methoxybutanoic acid), benzyl ester 2R,3R- and 2S,3S-2-Amino-3-methoxybutanoic acid, benzyl ester (177 mg, 0.79 mmol) are dissolved in dry dichloromethane (10 ml) and 2-ethoxy-N-ethoxycarbonyl-1,2-dihydroquinoline (195 mg, 0.79 mmol) and N-benzyloxycarbonyl-α-benzyl-δ-(L-α-aminoadipyl)-S-benzyl-L-cysteine (456 mg, 0.79 mmol), prpared as described by Baldwin et al, Journal of the Chemical Society, Perkin I, 1981, 2253), and sodium sulphate (100 mg) are added and the mixture stirred for 24 hours. The solution is evaporated, the residue is dissolved in ethyl acetate (150 ml), and the ethyl acetate solution washed in turn with 2M hydrochloric acid (50 ml), saturated sodium hydrogen carbonate solution (50 ml) and brine (50 ml), then dried, filtered and evaporated. Purification by chromatography on silica using ethyl acetate and hexane as consecutive eluants gives the title compound as a colourless solid (180 mg, 29%), m.p. 116°–118°; $[\alpha]_D^{20} -11.7°$ (c 1, CHCl$_3$) (the 2R,3R compound is less polar than the other, 2S,3S, isomer).

(6) δ-(L-α-Aminoadipyl)-L-cysteinyl-(2R,3R-2-amino-3-methoxybutanoic acid)

N-Benzyloxycarbonyl-α-benzyl-δ-(L-α-aminoadipyl)-S-benzyl-L cysteinyl-(2R,3R-2-amino-3-methoxybutanoic acid), benzyl ester (200 mg, 0.26 ml) is dissolved in tetrahydrofuran (10 ml) and dry liquid ammonia (30 ml). Sodium is added in small portions until a permanent blue colouration remains for 10 minutes and the solution is then quenched by the addition of dry ammonium sulphate until colourless. The solvent is evaporated, the residue is dissolved in 50 mM sulphuric acid (20 ml) and Hopkins reagent (0.05 ml, Baldin et al, ibid) is added. The pH is raised to 4 using ammonium hydroxide and the resultant precipitate is washed with water (3×20 ml), then suspended in water (10 ml) and treated with an excess of hydrogen sulphide. Filtration to remove mercuric sulphide and freeze drying gives the title compound[1] as a white solid (67 mg, 68%), $^1$H n.m.r (D$_2$O, referred to external tetramethylsilane—TMS, δ values, p.p.m) 1.05 (3H, d, J 8 Hz), 1.60–1.90 (4H, m), 2.25 (2H, t, J, 8 Hz), 2.80 (2H, m), 3.25 (3H, s), 3.75–3.90 (2H, m) and 4.40 (1H, m).

[1] The yield of the compound is estimated by the addition of a known quantity of dioxan, followed by n.m.r. integration of the standard against the 1.05 signal (the CHCH$_3$ protons). By this method a residual quantity of about 10% of ammonium salt is usually detected in the tripeptide. This contaminant will similarly yield the methoxylated penicillin upon incubation with isopenicillin N synthetase enzyme as described in Example 3.

Example 2

Preparation of δ-(L-α-aminoadipyl)-L-cysteinyl-(D-serine-O-methyl ether)

(1) N-p-Methoxybenzyloxycarbonyl-D-serine benzyl ester

N-p-Methoxybenzyloxycarbonyl-D-serine (5.39 mg, 2.00 mmol; prepared as a colourless solid of m.p. 96°–97° C. in 60% yield by the procedure of Weygand and Hunger, Berichte, 1962, 95 (1), 1) is dissolved in methanol and treated with a solution of potassium carbonate (138 mg, 1.00 mmol) in water (2 ml). The mixture is evaporated by dryness, N,N-dimethyl-formamide (DMF) is added and re-evaporated (2×2 ml), and the solid residue is then dissolved in dry warm DMF, benzyl bromide (248 µl, 2.1 mmol) is added and the solution is warmed in a dry closed flask at 50° C. for 1 hour. The resulting mixture is partioned between ether (10 ml) and water (10 ml) and the aqueous layter is extracted with ether (2×10 ml). The combined ether extracts are washed with saturated sodium bicarbonate (5 ml) and saturated brine (5 ml), dried and evaporated to dryness. The residue is purified on a column of silica gel using 1:1 v/v ethyl acetate:petroleum ether as eluant to yield to title compound as a homogenous oil (590 mg, 82%) which crystallises on standing to give a colourless solid of m.p. 67°–68° C. (from diethyl ether); $[\alpha]_D^{20} -6.3°$ (c 4.0, CHCl$_3$).

(2) N-p-Methoxybenzyloxycarbonyl-O-methyl-D-serine benzyl ester

The N-p-methoxybenzyloxycarbonyl-D-serine benzyl ester (720 mg, 2.00 mmol) is dissolved in dry dichloromethane (20 ml) and the solution cooled to dry ice/acetone. Boron trifluoride etherate (100 µl) is added followed by the portionwise addition of diazomethane (30 mmol in 20 ml CH$_2$Cl$_2$). After about 30 minutes the solution is filtered and washed once with water (10 ml), then dried (MgSO$_4$) and evaporated to dryness. The resulting residue is chromatographed on silica gel using chloroform as eluant to give the pure title compound as an oil (520 mg, 70%) which crystallises on standing to give a colourless solid of m.p. 68°–69° C.; $[\alpha]_D^{20} -1.3°$ (c 4.0, CHCl$_3$).

(3) O-Methyl-D-serine benzyl ester, hydrochloride

To N-p-methoxybenzyloxycarbonyl-O-methyl-D-serine benzyl ester (130 mg, 0.35 mmol) is added a mixture of cold trifluoroacetic acid (TFA): anisole (4.8:1 v/v) (0.6 ml). The mixture is shaken on an ice until all the solid has dissolved and the TFA is then evaporated initially on a rotary evaporator at 0° C., finally using a high vacuum pump. The resulting residue is purified by chromatograpy on silica gel using 98:2 v/v chloroform:methanol as eluant to give the title compound in basic form as a yellowish oil (38 mg, 55%); this is converted to the hydrochloride salt which is a white solid, m.p. 100°–101° C., $[\alpha]_D^{20}$ +15.5° (c 2.0, CH$_3$OH).

(4)

(N-Benzyloxycarbonyl-α-benzyl-δ-L-α-aminoadipyl)-(S-benzyl-L-cysteinyl)-(O-methyl-D-serine benzyl ester)

(N-Benzyloxycarbonyl-α-benzyl-δ-L-α-aminoadipyl)-S-benzyl-L-cysteine (150 mg, 0.26 mmol, prepared as described by Baldwin et al, ibid) and O-methyl-D-serine benzyl ester, hydrochloride salt, (63 mg, 0.26 mmol) are dissolved in dichloromethane (8 ml) containing triethylamine (36 μl, 0.26 mmol). 2-Ethoxy-N-ethoxycarbonyl-1,2-dihydroquinoline (64 mg) is added and the solution is stirred for 24 hours. The solution is then evaporated, the residue dissolved in chloroform (10 ml), the chloroform solution washed in turn with 0.1M hydrochloric acid (10 ml) and saturated sodium hydrogen carbonate solution (10 ml), dried (MgSO$_4$), filtered and evaporated. Purification by chromatography on silica gel using 98:2 v/v chlorform:methanol as eluant gives the title compound (150 mg, 76%) which is crystallised from ethyl acetate to give a colourless solid of m.p. 151°–152° C., $[\alpha]_d^{20}$ −13.9° (c 1.0, CHCl$_3$); $^1$H n.m.r (CD$_3$CN, referred to external TMS, δ value, p.p.m.) 1.5–2.3 (includes solvent peaks), 2.62 (2H, ABX octet, J$_{AB}$ 13.5, J$_{AX}$ 7.4 and J$_{BX}$ 5.0 Hz) 3.25 (3H, s), 3.56 (1H, A part of ABX, J$_{AB}$ 9.2, J$_{AX}$ 3.2 Hz), 3.73 (3H, s), 3.77 (1H, B part of ABX, J$_{BX}$ 4.0 Hz), 4.2, 4.52, 4.60 (3×1H, m), 5.1 (6H, m), 6.13, 6.68, 7.17 (3×1H), 7.35 (20H, m).

(5)

δ-(L-α-Aminoadipyl)-L-cysteinyl-(D-serine-O-methyl ether)

(N-Benzyloxycarbonyl-α-benzyl-δ-L-α-aminoadipyl)-(S-benzyl-L-cysteinyl)-(O-methyl-D-serine benzyl ester) (80 mg, 0.10 mmol) is dissolved in tetrahydrofuran (1 ml) and dry liquid ammonia (30 ml). Sodium is added in small portions until the solution is permanently blue for 5 minutes, the solution then being quenched with dry ammonium sulphate until colourless. The solvent is evaporated and the residue is dissolved in water (5 ml). Ammonium hydroxide is added to the solution to raise the pH to 8 and oxygen gas is then bubbled through it for 4 hours. Purification by preparative electrophoresis (pH 3.5, 3 Kv, 2 hours) gives the title compound in its disulphide form (10 mg, 26%) as a colourless solid, $^1$H n.m.r. (D$_2$O, referred to external TMS, δ values, p.p.m.) 1.5–1.8 (4H, m), 2.25 (2H, t, J 7.0 Hz) 2.73 (2H, m), 3.19 (3H, s), 3.65 (2H, ABX, J$_{AB}$ 10,5 J$_{AX}$ 3.9, J$_{BX}$ 5.5 Hz), 3.84 (1H, t, J 6.2 Hz), 4.40 (1H, t, J 5.8 Hz), 4.47 (1H, m).

EXAMPLE 3

Preparation of 2S-2-methoxy-2-methyl-6-δ-(L-α-aminoadipamido)-3-carboxypenam

δ-(L-α-Aminoadipyl)-L-cysteinyl-(2R,3R,-2-amino-3-methoxybutanoic acid (210 μg: prepared as described in Example 1) is incubated with purified isopenicillin N synthetase (1.1 units, obtained as described below) in the presence of the cofactors dithiothreitol (2.11 mM), ascorbic acid (1.06 mM), ferrous sulphate (0.11 mM) and catalase (bovine liver, 1800 sigma units) in tris-HCl buffer (50 mM, p 7.5; tris stands for 2-amino-2-hydroxymethylpropane 1,3-diol) to a total volume of 1 ml, the incubation being carried out at 27° C. in a shaker (250 r.p.m.) with exposure exposed to the air for 30 minutes. The protein is precipitated from the mixture by the addition of acetone to a concentration of 70% by volume of acetone, then separated by centrifugation and the supernatant freeze dried. The freeze dried material is redissolved in water (500 μl) and the product purified by HPLC (Waters:Z Module Radial Compression Separator System with Radial-Pak C$_{18}$10 cartridge) using 90% 50 mM KH$_2$PO$_4$/10% methanol by volume as the eluting solvent and detecting the antibiotic by its absorption at 220 mm. The product which is thus obtained is freeze dried immediately to provide the title compound.

The freeze dried material has the following the n.m.r. spectrum, the assignment of the various signals to protons in the structure (IV) shown hereinbefore being as follows:

| Signal | Protons |
| --- | --- |
| 1.47 | γ-CH$_2$— |
| 1.64 | β-CH$_2$— |
| 1.74 | CH$_3$— at C-2 |
| 2.15 | δ-CH$_2$ |
| 3.13 | CH$_3$O— at C-2 |
| 3.49 | α-CH— |
| 4.24 | H-3 |
| 5.16 | H-5 |
| 5.32 | H-6 |

Nuclear Overhauser experiments confirm the stereochemistry of the compound at the 2-position as indicated in the title of the Example. Thus, irradiation of the singlet at 1.74 p.p.m. (methyl group) gives an enhancement (typically 19%) in the difference spectrum of the signal at 4.24 p.p.m. (H-3) which is consistent with a methyl group in the β-configuration (for Isopen N and Pen G the corresponding enhancement observed on irradiation of a β-methyl group is typically 21 and 25%, respectively). The mass spectrum of the compound obtained under Fast Atom Bombardment (FAB) conditions shows a molecular ion [MH+] 376 m/e. The base peak in the spectrum at 321 m/e is a characteristic penicillin fragment:

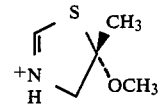

PREPARATION OF PURIFIED ISOPENICILLIN N SYNTHETASE

Cells of Cephalosporin acremonium CO728 are grown as described by Fawcett et al, (Biochem. J., 1976, 157, 651–660) with the variation that distilled water is used instead of tap water. The isopenicillin N synthetase is isolated in purified form by the following steps, which are carried out at 2°–4° C.

(1) Preparation of the crude extract

Mycelia (96 hours old/about 10 hours from the beginning of stationary phase) are harvested by filtration through a double-layer of cheese cloth. The cells collected are resuspended in 3×(v/w) distilled water and suction-dried through Whatman filter paper (No. 52) in a Bucher funnel. The suction-dried mycelia are suspended in approximately 3×(v/w) of 50 mM Tris-HCl buffer, pH 8.0, and disrupted in a Dyno Mill (Willy A Bacofen AG Maschinenfabrik, Basel) with 500 ml of 0.25 mm glass beads, being stirred at 3000 r.p.m. in the 600 ml glass head.

(2) Protamine sulphate fractionation

To the above homogenate, a one fifth volume of protamine sulfate solution (6% w/v in distilled water) is added. The resulting solution is stirred for 20 minutes and centrifuged at 10,000 g for 30 minutes to remove precipitate.

(3) Ammonium sulphate fractionation

The supernatant collected above is brought to 55% saturation with ammonium sulphate (Sigma Grade I) and the precipitate is removed by centrifugation at 10,000 g for 30 minutes. The supernatant is then brought to 85% saturation with ammonium sulphate and enzyme protein is recovered as a precipitate after centrifugation at 10,000 g for 45 minutes.

(4) Sephadex G75 column chromatography

The precipitate obtained after 55-85% ammonium sulphate fractionation is dissolved in a minimum amount of Tris-HCl buffer (50 mM, pH 7.5, 0.015% w/v sodium azide), the final protein concentration being about 40 mg/ml. 80 ml of this protein solution is loaded onto a Sephadex G-75 (Pharmacia, coarse) column (3.7 cm×110 cm) which has been pre-equilibrated with the same Tris-HCl buffer. The fractions with isopenicillin N synthetase activity are pooled and enzyme protein is concentrated by precipitation with 85% w/v ammonium sulphate followed by centrifugation at 10,000 g for 45 minutes.

(5) DEAE Sepharose CL-6B column chromatography

A highly purified enzyme preparation is obtained through ion-exchange chromatography of the enzyme fractions from Sephadex G75 column chromatography. The active fractions are pooled and loaded directly onto a DEAE-Sepharose CL-6B column (5 cm×11.5 cm) which has been pre-equilibrated with Tris-HCl buffer (50 mM, pH 7.5, 0.015% w/v sodium azide). The column is washed with about 500 ml of 50 mM NaCl in the same Tris-HCl buffer to remove unbound material. The column is then subjected to a gradient elution of NaCl in buffer (50 mM→250 mM, total volume 800 ml, linear gradient), enzyme activity being eluted at about 100 mM NaCl. The preparation of the enzyme as obtained from the column is suitable for direct use.

The activity of an amount of the enzyme may be quantitatively expressed in units of isopenicillin N synthetase activity, one each unit being defined as that amount of enzyme activity required to form $1\mu$ mole of isopenicillin N per minute at 27° C. in a standard assay procedure employing incubation conditions similar to those described above.

Example 4

Preparation of 2-methoxy-6-δ-(L-α-aminoadipamido)-3-carboxypenam

δ-(L-α-Aminoadipyl)-L-cysteinyl-(D-serine-O-methyl ether), prepared as described in Example 2, is incubated with purified isopenicillin N synthetase obtained as described under Example 3, the incubation medium being constituted as follows with the various component solutions being prepared in water.

| | |
|---|---|
| Tripeptide (10 mg/ml) | 100 µl |
| Isopenicillin N synthetase | 6.6 units |
| Ferrous sulphate (5 mM) | 100 µl |
| L-Ascorbic acid (5 mM) | 100 µl |
| Dithiothreitol (100 mM) | 50 µl |
| Catalase (standard preparation, 1/10 diluted) | 43 µl |
| Sodium hydroxide (100 mM) | 30 µl |

The final volume is adjusted to 5 ml with pH 7.5 tris buffer. A control is run in which 100 µl of water replaces the peptide solution. The incubation is carried out at 30° C. in a shaker (250 r.O.m) with exposure to the air for 30 minutes. The protein is precipitated from the mixture by the addition of acetone to a concentration of 70% by volume of acetone, then separated by centrifugation (5,000 r.p.m. for 10 minutes) and the supernatant freeze dried after removal of the acetone in vacuo to give the title compound which is believed to be a mixture of the 2R and 2S-isomers.

The freeze dried material has a $^1H$ n.m.r. spectrum (250 MHz in $D_2O$ with HOD suppression, referenced to external TMS, δ values, p.p.m.) showin ghe AB-quartet at 5.23, 5.45 (2H, J=3.95 Hz).

Example 5

Bioassay tests (1)

2S-2-Methoxy-2-methyl-6-δ-(L-α-aminoadipamido)-3-carboxypenam

The freeze dried product obtained from 210 µg of tripeptide as described in Example 3 was dissolved in pH 7.5 tris buffer to give a solution with a total volume of 1 ml. 100 µl of this solution was used for hole-plate inhibition assay for various as micro-organisms as listed in Table 1, the antibiotic activity of the penicillin against these micro-organisms being clearly illustrated by the results given in the table. Also indicated in the table are the amounts of isopenicillin N required to give similar levels of inhibition for each particular micro-organism and it will be seen that the activity of the penicillin 2S-2-methoxy-2-methyl-6-δ-(L-α-aminoadipamido)-3-carboxypenam is broadly comparable to that of isopenicillin on the basis of a 50% conversion rate from the tripeptide.

TABLE 1

| Micro-organisms | Diameter of inhibition produced (mm)* | Isopenicillin N equivalent (µg/ml) |
|---|---|---|
| *Pseudomonas aeruginosa* | diffuse halo only | >60 |
| *Bacillus megaterium* | 17 | >80 |
| *Staphylococcus aureus* | 28 | >100 |
| *Escherichia coli* | 20 | >10 |
| *Escherichia coli* with added β-lactamase | — | — |
| *Salmonella typhimunun* | 17 | >100 |
| *Alcalgines faecalis* | — | — |
| *Klebsiella aerogenes* | — | — |

*A negative sign indicates the absence of inhibition.

(2)

2-Methoxy-6-δ-(L-α-aminoadipamido)-3-carboxypenam

The freeze dried product obtained from 500 µg of tripeptide as described in Example 4 was redissolved in 200 µl of water and 100 µl of this solution was incubated by hole-poate assay against *S. aureus* (both with and without the addition of β-lactamase I from *Bacillus cereus* 569/H/9. The remaining 100 μl of solution was diluted with another 100 μl of water and 100 μl of this more dilute solution was also assayed against *S. aureus*. This procedure was repeated to give successive levels of dilution. A control was used which contained none of the freeze dried solid. The results obtained are shown in the following Table 2 from which it will be seen that the antibiotic activity of the compound, which is clearly expressed in the absence of the β-lactamase, is destroyed by the action of this enzyme.

TABLE 2

| Dilution | Weight of substrate by reference to amounts of starting tripeptide (μg) | Diameter of inhibition produced (mm)* | | |
|---|---|---|---|---|
| | | β-lactamase absent | β-lactamase present | Control |
| 1x | 500 | 30 | — | — |
| 2x | 250 | 26 | — | — |
| 4x | 125 | 21 | — | — |
| 8x | 62.5 | 17 | — | — |
| 16x | 31.25 | 14 | — | — |

*A negative sign indicates the absence of a inhibition.

I claim:

1. A compound of formula I or a physiologically acceptable salt thereof-wherein X represents sulphur or methylene, R represents hydrogen, amino or an acylated or carbamylated amino group, $R_2$ represents hydrogen or an alkyl group and $R_3$ represents an alkoxy group.

2. A compound according to claim 1, in which X represents a methylene group.

3. A compound according to claim 1, in which $R_1$ represents an amino group.

4. A compound according to claim 1, in which $R_2$ represents an alkyl group.

5. A compound according to claim 4, in which $R_2$ represents an alkyl group which contains 1-5 carbon atoms.

6. A compound according to claim 5, in which $R_2$ represents methyl or ethyl.

7. A compound according to claim 1, in which $R_3$ represents an alkoxy group containing 1-5 carbon atoms.

8. A compound according to claim 1, in which $R_3$ represents methoxy, ethoxy, propoxy or isopropoxy.

9. A compound according to claim 1, in the form of a physiologically acceptable salt.

10. A compound according to claim 1, in which $R_3$ has a spatial disposition which is similar to that of the 3-carboxyl group with respect to the general plane of the penam ring system.

11. A compound according to claim 1, in which X represents sulphur or methylene, $R_1$ represents hydrogen or amino, $R_2$ represents hydrogen, methyl or ethyl and $R_3$ represents methoxy or ethoxy.

12. A compound according to claim 1 which is 2-methoxy-2-methyl-6-δ-(L-α-aminoadipamido)-3-carboxypenam, 2-methoxy-2-methyl-6-δ(D-α-aminoadipamido)-3-carboxypenam, 2-methoxy-2-methyl-6-δ-adipamido-3-carboxypenam and 2-methoxy-2-methyl-6-δ-(L-S-carboxymethylcysteinyl)-3-carboxypenam, 2-methoxy-6-δ-(L-α-aminoadipamido)-3-carboxypenam, 2-methoxy-6-δ-(D-α-aminoadipamido)-3-carboxypenam, 2-methoxy-6-δ-adipamido-3-carboxypenam or 2-methoxy-6-δ-(L-S-carboxymethylcysteinyl)-3-carboxypenam.

13. A compound according to claim 12 in which the 2-methoxy group has an S configuration.

14. A pharmaceutical composition useful for treating bacterial infections in humans and animals which comprises an antibacterially effective amount of a compound of the formula (I):

wherein X is sulphur or methylene; $R_1$ is hydrogen, amino, acylated amino or carbamylated amino; $R_2$ is hydrogen or alkyl; and $R_3$ is alkoxy, in combination with a pharmaceutically acceptable carrier.

15. A composition according to claim 14, in dosage form.

16. A composition according to claim 14 wherein X is methylene.

17. A composition according to claim 14 wherein $R_1$ is amino.

18. A method of treating bacterial infections in humans and animals which comprises administering to a human or animal in need thereof an antibacterially effective amount of a compound of the formula (I):

wherein X is sulphur or methylene; $R_1$ is hydrogen, amino, acylated amino or carbamylated amino; $R_2$ is hydrogen or alkyl; and $R_3$ is alkoxy, in combination with a pharmaceutically acceptable carrier.

19. A method according to claim 18 wherein X is methylene.

20. A method according to claim 18 wherein $R_1$ is amino.

* * * * *

UNITED STATES PATENT AND TRADEMARK OFFICE
CERTIFICATE OF CORRECTION

PATENT NO. : 4,722,924

DATED : February 2, 1988

INVENTOR(S) : JAMES EDWARD BALDWIN

It is certified that error appears in the above-identified patent and that said Letters Patent is hereby corrected as shown below:

Correct item [21] Appl. No. by changing "766,429" to -- 768,429 --.

Signed and Sealed this

Eighteenth Day of July, 1989

*Attest:*

DONALD J. QUIGG

*Attesting Officer*  *Commissioner of Patents and Trademarks*